United States Patent
Casanello et al.

(10) Patent No.: US 7,576,113 B2
(45) Date of Patent: Aug. 18, 2009

(54) USE OF (E)-5-(4-CHLORBENZYLIDEN)-2,2-DIMETHYL-1-(1H-1,2,4-TRIAZOL-1-YLMETHYL) CYCLOPENTANOL FOR COMBATING RUST ATTACKS ON SOYA PLANTS

(75) Inventors: Diego Lopez Casanello, Speyer (DE); John-Bryan Speakman, Bobenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 159 days.

(21) Appl. No.: 11/628,057

(22) PCT Filed: Jun. 16, 2005

(86) PCT No.: PCT/EP2005/006499

§ 371 (c)(1),
(2), (4) Date: Nov. 30, 2006

(87) PCT Pub. No.: WO2005/122771

PCT Pub. Date: Dec. 29, 2005

(65) Prior Publication Data

US 2008/0064601 A1      Mar. 13, 2008

(30) Foreign Application Priority Data

Jun. 17, 2004   (DE) .................. 10 2004 029 338

(51) Int. Cl.
*A01N 43/653* (2006.01)
*A61K 31/41* (2006.01)
(52) U.S. Cl. .................................. 514/383; 504/272
(58) Field of Classification Search ............... 504/272; 514/383

See application file for complete search history.

(56) References Cited

U.S. PATENT DOCUMENTS 5,246,953 A * 9/1993 Greiner et al. ............. 514/383

FOREIGN PATENT DOCUMENTS

| CA | 2 437 183 A1 | 2/2005 |
|----|--------------|--------|
| WO | WO-02/21913 A1 | 3/2002 |
| WO | WO-02/051246 A1 | 7/2002 |

* cited by examiner

*Primary Examiner*—Johann R Richter
*Assistant Examiner*—Andriae M Holt
(74) *Attorney, Agent, or Firm*—Birch, Stewart, Kolasch & Birch, LLP

(57) ABSTRACT

The invention relates to the use of triticonazole for controlling rust disease on soybeans and to a method for controlling rust disease in soybeans, in which the soybean plants and/or their seed are treated with an effective amount of triticonazole.

20 Claims, No Drawings

USE OF (E)-5-(4-CHLORBENZYLIDEN)-2,2-DIMETHYL-1-(1H-1,2,4-TRIAZOL-1-YLMETHYL) CYCLOPENTANOL FOR COMBATING RUST ATTACKS ON SOYA PLANTS

This application is a national stage application for PCT/EP05/06499 filed under 35 U.S.C. 371, filed Jun. 16, 2005

Use of (E)-5-(chlorobenzylidene)-2,2-dimethyl-1(1H-1,2,4-triazol-1-yl-methyl)cyclopentanol for controlling rest disease on soybean plants The invention relates to the use of (E)-5-(4-chlorobenzylidene)-2,2-dimethyl-1-(1H-1,2,4-triazol-1-ylmethyl)cyclopentanol for controlling rust disease on soybean plants.

Until recently, the main growing areas for soybean cultures were free from diseases caused by harmful fungi, such as rust, which were of economical importance. However, in 2001 and 2002, South America saw increasingly serious rust diseases in soybean cultures caused by the harmful fungi *Phakopsora pachyrhizi* and *Phakopsora meibomiae*. The results were considerable harvest and yield losses.

Most current fungicides are not suitable for controlling rust diseases in soybean cultures because they do not sufficiently inhibit the multiplication of the harmful fungi which cause the rust disease, such as *Phakopsora pachyrhizi* and *Phakopsora meibomiae*. Moreover, there is a risk of the fungicidal active ingredient adversely affecting the symbiosis of root nodule bacteria (Rhizobium and Bradyrrhizobium) and soybean plants, thus causing yield loss.

CA 2,437,183 describes the use of strobilurins for the treatment of rust diseases on legumes.

However, there is a basic need for providing further active ingredients against certain fungal diseases to avoid the development of resistance.

It was therefore an object to provide a further agent which makes possible an effective control of rust diseases on soybean plants. In particular, the agent should have no adverse effect on the symbiosis of root nodule bacteria and soybean plants.

Surprisingly, it has now been found that (E)-5-(4-chlorobenzylidene)-2,2-dimethyl-1-(1H-1,2,4-triazol-1-ylmethyl)cyclopentanol efficiently inhibits the multiplication of the abovementioned harmful fungi and is thus suitable for controlling the rust disease on soybean plants which is caused by these harmful fungi.

The invention therefore relates to the use of (E)-5-(4-chlorobenzylidene)-2,2-dimethyl-1-(1H-1,2,4-triazol-1-ylmethyl)cyclopentanol for controlling rust disease on soybean plants and to a method for controlling rust disease on these plants in which the plant which requires such a treatment, or parts of this plant or the soil which is intended for culturing or growing the plant, is treated with (E)-5-(4-chlorobenzylidene)-2,2-dimethyl-1-(1H-1,2,4-triazol-1-ylmethyl)cyclopentanol.

The use of (E)-5-(4-chlorobenzylidene)-2,2-dimethyl-1-(1H-1,2,4-triazol-1-yl-methyl)cyclopentanol efficiently prevents infection of the soybean plants with rust disease (protective treatment) and, moreover, also leads to a cure for plants which are already diseased (curative treatment).

Surprisingly, rust disease of soybean plants can also be prevented efficiently by treating the seed with (E)-5-(4-chlorobenzylidene)-2,2-dimethyl-1-(1H-1,2,4-triazol-1-yl-methyl)cyclopentanol.

Moreover, it has unexpectedly emerged that the symbiosis of the root nodule bacteria with the soybean plants is not, or at least not substantially, adversely affected by the application of (E)-5-(4-chlorobenzylidene)-2,2-dimethyl-1-(1H-1,2,4-triazol-1-yl-methyl)cyclopentanol.

Both the racemate of (E)-5-(4-chlorobenzylidene)-2,2-dimethyl-1-(1H-1,2,4-triazol-1-yl-methyl)cyclopentanol and its enantiomers and nonracemic mixtures of these enantiomers are suitable in accordance with the invention. (E)-5-(4-Chlorobenzylidene)-2,2-dimethyl-1-(1H-1,2,4-triazol-1-ylmethyl)cyclopentanol is known to the skilled worker under the name triticonazole and commercially available.

The term "plant parts" here and hereinbelow refers not only to the aerial plant parts such as foliage, but also to the subterranean plant parts, i.e. the root system, and to the fruits and seeds.

To control the rust disease, the soybean plants, or the plant parts to be protected from rust disease, or the soil, are treated with such an amount of an active ingredient preparation comprising triticonazole as is necessary for controlling the rust disease. The way in which the active ingredient preparation is applied depends in a known manner on the intended use and the type of application. Expediently, the type of active ingredient preparation is chosen in such a way that a fine and uniform distribution of the active ingredient(s) is ensured.

In a first preferred embodiment of the invention, the aerial plant parts of the soybean plants, in particular the leaves, are treated with a suitable preparation of the active ingredient. Preferably, triticonazole is employed in an aqueous spray mixture.

As a rule, the triticonazole application rates required for protective treatment of the aerial plant parts amount to 10 to 1000 g/ha, in particular to 20 to 500 g/ha.

As a rule, the triticonazole application rates required for curative treatment of the aerial plant parts amount to 10 to 1000 g/ha, in particular to 20 to 500 g/ha.

In another embodiment of the invention, the seed is treated with a preparation of the active ingredient which is suitable for seed treatment. Active ingredient preparations for seed treatment are, in particular, aqueous spray mixtures, ready-to-use dusts and ULV solutions. In the case of seed treatment, triticonazole is generally employed in an amount of from 1 to 500 g, preferably 10 to 200 g, per 100 kilograms of seed.

Moreover, other harmful fungi which are frequently found in soybean plants can also be controlled very effectively with the method according to the invention. The most important fungal diseases in soybeans are listed hereinbelow:

damping-off caused by *Rhizoctonia solani*,
stem rot caused by *Fusarium solani*,
stem rot caused by *Fusarium* spp.,
stem and pod blight caused by *Phomopsis phaseoli*+spp.,
purple blotch caused by *Cercospora kikuchi*,
frogeye leaf spot caused by *Cercospora sojina*,
seedling blight caused by *Pythium* spp.,
stem antrachnose caused by *Colletotrichum demativum* var. *truncata*,
brown spot caused by *Septoria glycines*,
leaf spot caused by *Cercospora* spp.,
powdery mildew caused by *Erysiphe polygoni*.

To widen the spectrum of action, triticonazole can also be employed together with other active ingredients which are used in soybean growing, for example together with herbicides, insecticides, nematicides, growth regulators, fungicides or else fertilizers.

The following list of active ingredients with which triticonazole can be used in accordance with the invention is intended to illustrate the possible combinations, but not to impose any limitation:

Fungicides:

acylalanines, in particular oxadixyl;

amine derivatives, in particular guazatine, iminoctadine;

azoles, in particular difenoconazole, epoxyconazole, fenbuconazole, fluquiconazole, flusilazol, flutriafol, hexaconazole, imazalil, metconazole, myclobutanil, penconazole, propiconazole, prochloraz, prothioconazole, tebuconazole;

dicarboximides such as iprodion, procymidon, vinclozolin;

heterocylic compounds such as anilazin, benomyl, boscalid, carbendazim, carboxin, oxycarboxin, cyazofamid, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazol, triforine;

nitrophenyl derivatives such as binapacryl, dinocap, dinobuton, nitrophthal-isopropyl;

phenylpyrroles such as fenpiclonil or fludioxonil;

sulfur;

other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl aluminum, iprovalicarb, hexachlorobenzene, metrafenon, pencycuron, propamocarb, phthalide, toloclofos-methyl, quintozene, zoxamid;

strobilurins such as azoxystrobin, dimoxystrobin, fluoxastrobin, kresoxim-methyl, metominostrobin, orysastrobin, picoxystrobin, pyraclostrobin or trifloxystrobin;

sulfenic acid derivatives such as captafol, captan, dichlofluanid, folpet, tolyflluanid cinnamamides and analogs such as dimethomorph, flumetover or flumorph.

Insecticides/acaricides:

organo(thio)phosphates, in particular acephate;

carbamates, in particular alanycarb, benfuracarb, bendiocarb, carbosulfan, fenoxycarb, furathiocarb, methiocarb, methomyl, thiodicarb, triazamate;

pyrethroids such as allethrin, bifenthrin, cyfluthrin, cyphenothrin, cypermethrin and the alpha-, beta-, theta- and zeta isomers, deltamethrin, esfenvalerate, ethofenprox, fenpropathrin, fenvalerate, cyhalothrin, lambda-cyhalothrin, imiprothrin, permethrin, prallethrin, pyrethrin I, pyrethrin II, silafluofen, taufluvalinate, tefluthrin, tetramethrin, tralomethrin, transfluthrin, zeta-cypermethrin;

neonicotinoids such as flonicamid, clothianidin, dinotefuran, imidacloprid, thiamethoxam, nitenpyram, nithiazin, acetamiprid, thiacloprid;

pyrazole insecticides such as acetoprole, ethiprole, fipronil, tebufenpyrad, tolfenpyrad and vaniliprole;

and also spinosad and thiamethoxam.

Growth regulators such as chlormethquat and mepiquat.

Mixtures of triticonazole with a further fungicide from the azole fungicide group have proved to be very especially suitable for the use according to the invention. Preferred azole fungicides are epoxyconazole, tebuconazole, fluquinconazole, flutriafol, metconazole, myclobutanil, cycproconazole, prothioconazole and propiconazole. By applying triticonazole jointly with a further azole fungicide, an increased activity is obtained so that in total lower application rates of fungicides are required for obtaining the desired fungicidal effect.

If triticonazole is employed together with an azole fungicide, the active ingredients will preferably be employed in a triticonazole to azole fungicide weight ratio of from 1:100 to 100:1 and in particular 1:20 to 20:1. In this case, the application rates of further azole fungicide preferably amount to from 1 to 500 g/ha and in particular to 5 to 300 -g/ha.

Likewise especially suitable for the use according to the invention are mixtures of triticonazole with at least one further fungicide from the strobilurin group which is selected from among trifloxystrobin, pyraclostrobin, orysastrobin, fluoxastrobin and azoxystrobin.

If triticonazole is employed together with one of the above-mentioned strobilurins, the active ingredients will preferably be employed in a triticonazole to strobilurin weight ratio of from 1:100 to 100:1 and in particular 1:20 to 20:1. In this case, the application rates of strobilurin preferably amount to from 1 to 500 -g/ha and in particular to 5 to 300 -g/ha.

If triticonazole is employed jointly with a further fungicidal active ingredient, the latter can be applied simultaneously with triticonazole or after a short time interval, for example within a few days before or after the triticonazole treatment. In the case of simultaneous application, the treatment of the soybean plant can be effected in one pass where a composition comprising triticonazole and the further fungicidal active ingredients are applied, or else in separate passes where different compositions of the individual active ingredients are applied.

It has furthermore been proved to be particularly advantageous to employ triticonazole together with at least one active ingredient against stinging or sucking insects and other arthropods, for example of the order Coleoptera, in particular *Phyllophaga* sp. such as *Phyllophaga cuyabana*, *Sternechus* sp. such as *Sternechus pingusi*, *Stemechuns subsignatus*, *Promecops* sp. such as *Promecops carinicollis*, *Aracanthus* sp. such as *Aracanthus morei*, and *Diabrotica* sp. such as *Diabrotica speciosa*, *Diabrotica longicornis*, *Diabrotica* 12-*punctata*, *Diabrotica virgifera*, Lepidoptera in particular *Elasmopalpus* sp. such as *Elasmopalpus lignosellus*, Isoptera, in particular *Rhinotermitida*, Homoptera, in particular *Dalbulus maidis* or against nematodes, including root knot nematodes, for example *Meloidogyne* spp. such as *Meloidogyne hapla*, *Meloidogyne incognita*, *Meloidogyne javanica*, and other *Meloidogyne* species; cyst-forming nematodes such as *Globodera rostochiensis* and other *Globodera* species; *Heterodera avenae*, *Heterodera glycines*, *Heterodera schachtii*, *Heterodera trifolii*, and other *Heterodera* species; gall nematodes, for example *Anguina* species; stem eel worms and foliar nematodes such as *Aphelenchoides* species.

In particular, it has proved useful to employ triticonazole together with at least one insecticide from the neonicotinoid group, specifically with imidacloprid, thiametoxam or clothiamidin, or an insecticide from the group of the pyrazole insecticides, specifically with fipronil.

In particular, it has proved useful to employ triticonazole together with an insecticide, in particular a neonicotinoid or pyrazole insecticide, for the treatment of seed or the treatment of seedlings of the soybean plants.

If triticonazole is employed jointly with a further insecticidal active ingredient, the latter can be applied simultaneously with triticonazole or after a short time interval, for example within a few days before or after the triticonazole treatment. In the case of simultaneous application, the treatment of the soybean plant can be effected in one pass where a composition comprising triticonazole and the further insecticidal active ingredient are applied, or else in separate passes where different compositions of the individual active ingredients are applied.

Since triticonazole has no adverse effect on the symbiosis of the root nodule bacteria and the soybean plants, the treatment of the seed with the active ingredient can be carried out simultaneously or within a narrow time interval around the infection of the seed with the root nodule bacteria. For example, the active ingredient can be applied to the seed jointly with a suitable preparation of the root nodule bacteria, for example an aqueous suspension of the root nodule bacteria.

Triticonazole and optionally the further active ingredient(s) can be used as such, in the form of their formulations or the use forms prepared therefrom, for example in the form of directly sprayable solutions, powders, suspensions or dispersions, emulsions, oil dispersions, pastes, dusts, compositions for broadcasting, or granules. Application is typically achieved by means of spraying, atomizing, dusting, broadcasting or pouring. In any case, the use forms and means should ensure the finest possible distribution of the active ingredients according to the invention.

Aqueous use forms of the active ingredients can be prepared from commercially available formulations of the active ingredients, for example from emulsion concentrates, pastes or wettable powders (sprayable powders, oil dispersions), by addition of water. To prepare emulsions, pastes or oil dispersions, the substances, as such or dissolved in an oil or solvent, can be homogenized in water by means of wetter, sticker, dispersant or emulsifier. However, it is also possible to prepare concentrates which consist of active substance, wetter, sticker, dispersant or emulsifier and, if appropriate, solvent or oil, and such concentrates are suitable for dilution with water.

The concentration of triticonazole and the optional further active ingredient(s) in the ready-to-use preparations can vary within substantial ranges. In general, they are between 0.0001 and 10%, preferably between 0.001 and 1% (% by weight total active ingredients, based on the total weight of the ready-touse formulation).

Triticonazole and the optional further active ingredient(s) can also be used successfully in the ultra-low-volume method (ULV), it being possible to apply formulations comprising more than 95% by weight of active ingredient, or indeed the active ingredient without additives.

Various types of oils or wetters, adjuvants, herbicides, fungicides, insecticides, nematicides, but also other pesticides, for example bactericides, can be added to the active ingredients, if appropriate also immediately prior to application (tank mix). These agents can be admixed to the compositions according to the invention in a weight ratio of from 1:10 to 10:1.

The formulations are prepared in the known manner, for example by extending the active ingredient with solvents and/or carriers, if appropriate using surfactants, i.e. emulsifiers and/or dispersants.

Solvents/carriers which are suitable are essentially:

water, aromatic solvents (e.g. Solvesso products, xylene), paraffins (for example mineral oil fractions), alcohols (for example methanol, butanol, pentanol, benzyl alcohol), ketones (for example cyclohexanone, methyl hydroxybutyl ketone, diacetone alcohol, mesityl oxide, isophorone), lactones (for example gamma-butyrolactone), pyrrolidones (pyrrolidone, N-methylpyrrolidone, N-ethylpyrrolidone, n-octylpyrrolidone), acetates (glycol diacetate), glycols, dimethyl fatty acid amides, fatty acids and fatty acid esters. In principle, solvent mixtures may also be used.

Carriers such as ground natural minerals (for example kaolins, clays, talc, chalk) and ground synthetic minerals (for example highly-disperse silica, silicates); emulsifiers such as nonionic and anionic emulsifiers (for example polyoxyethylene fatty alcohol ethers, alkylsulfonates and arylsulfonates), and dispersants such as lignin-sulfite waste liquors and methylcellulose.

Suitable surfactants are alkali metal salts, alkaline earth metal salts and ammonium salts of lignosulfonic acid, naphthalenesulfonic acid, phenolsulfonic acid, dibutyinaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenyl polyglycol ether, tributylphenyl polyglycol ether, tristerylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable and animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, mesityl oxide, isophorone, strongly polar solvents, for example dimethyl sulfoxide, 2-pyrrolidone, N-methylpyrrolidone, butyrolactone, or water.

Powders, materials for spreading and dusts can be prepared by mixing or jointly grinding the active substances with a solid carrier.

Granules, for example coated granules, impregnated granules and homogeneous granules, can be prepared by binding the active ingredients onto solid carriers. Solid carriers are, for example, mineral earths such as silica gels, silicates, talc, kaolin, Attaclay, limestone, lime, chalk, bole, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and plant products such as cereal meal, tree bark meal, wood meal and nutshell meal, cellulose powder and other solid carriers.

In general, the formulations comprise between 0.01 and 95% by weight, preferably between 0.1 and 90% by weight, in particular from 5 to 50% by weight, of the active ingredient. In this context, the active ingredients are employed in a purity of from 90% to 100%, preferably 95% to 100% (according to NMR spectrum).

Examples of formulations are:

1. Products for Dilution in Water

A) Water-soluble concentrates (SL)

10 parts by weight of triticonazole are dissolved in water or a water-soluble solvent. Alternatively, wetters or other adjuvants are added. Upon dilution in water, the active ingredient dissolves.

B) Dispersible concentrates (DC)

20 parts by weight of triticonazole are dissolved in cyclohexanone with addition of a dispersant, for example polyvinylpyrrolidone. Upon dilution in water, a dispersion results.

C) Emulsifiable concentrates (EC)

15 parts by weight of triticonazole are dissolved in xylene with addition of calcium dodecylbenzenesulfonate and castor oil ethoxylate (in each case 5%). Upon dilution in water, an emulsion results.

D) Emulsions (EW, EO)

40 parts by weight of triticonazole are dissolved in xylene with addition of calcium dodecylbenzenesulfonate and castor oil ethoxylate (in each case 5%). This mixture is introduced into water by means of an emulsifier (Ultraturrax) and made into a homogeneous emulsion. Upon dilution in water, an emulsion results.

E) Suspensions (SC, OD)

20 parts by weight of triticonazole are comminuted in a stirred ball mill with addition of dispersants, wetters and water or an organic solvent to give a fine suspension of active ingredient. Upon dilution in water, a stable suspension of the active ingredient results.

F) Water-dispersible and water-soluble granules (WG, SG)

50 parts by weight of triticonazole are ground finely with addition of dispersant and wetters and made into water-dispersible or water-soluble granules by means of technical apparatuses (for example extrusion, spray tower, fluidized bed). Upon dilution in water, a stable dispersion or solution of the active ingredient results.

G) Water-dispersible and water-soluble powders (WP, SP)

75 parts by weight of triticonazole are ground in a rotor-stator mill with addition of dispersants, wetters and silica gel. Upon dilution in water, a stable dispersion or solution of the active ingredient results.

2. Products for Direct Application

H) Dusts (DP)

5 parts by weight of triticonazole are ground finely and mixed intimately with 95% finely particulate kaolin. This gives a dust.

I) Granules (GR, FG, GG, MG)

0.5 part by weight of triticonazole is ground finely and combined with 95.5% carriers. Current methods are extrusion, spray drying or the fluidized bed. This gives granules for direct application.

J) ULV solutions (UL)

10 parts by weight of triticonazole are dissolved in an organic solvent, for example xylene. This gives a product for direct application.

Compositions which are useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Dusts and dustable powders (DP, DS)

Preferred FS formulations of triticonazole for seed treatment usually comprise from 0.5 to 80% of the active ingredient, from 0,05 to 5% of a wetter, from 0.5 to 15% of a dispersing agent, from 0.1 to 5% of a thickener, from 5 to 20% of an anti-freeze agent, from 0,1 to 2% of an anti-foam agent, from 1 to 20% of a pigment and/or a dye, from 0 to 15% of a sticker/adhesion agent, from 0 to 75% of a filler/vehicle, and from 0,01 to 1% of a preservative.

Suitable pigments or dyes for seed treatment formulations of triticonazole are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Wetters and dispersants, which are suitable are in particular the aforementioned surfactants. Preferred wetting agents are alkylnaphthaline sulfonates such as diisopropyl- or diisobutylnaphthalenesulfonates. Preferred dispersants are nonionic or anionic dispersants or mixtures of nonionic or anionic dispersants. Suitable nonionic dispersants which are employed are, in particular, ethylene oxide/propylene oxide block polymers, alkylphenol polyglycol ethers and tristryrylphenol polyglycol ethers, for example polyoxyethylene octylphenol ether, ethoxylated isooctylphenol, octylphenol, nonylphenol, alkylphenol polyglycol ether, tributylphenyl polyglycol ether, tristerylphenyl polyglycol ether, alkylarylpolyether alcohols, alcohol and fatty alcohol ethylene oxide condensates, ethoxylated castor oil, polyoxyethylene alkyl ether, ethoxylated polyoxy-propylene, lauryl alcohol polyglycol ether acetal, sorbitol esters and methyl cellulose. Suitable anionic dispersants which are used are, in particular, alkali metal, alkaline earth metal and ammonium salts of ligninsulfonic acid, naphthalenesulfonic acid, phenolsulfonic acid, dibutyinaphthalenesulfonic acid, alkylarylsulfonates, alkyl sulfates, alkylsulfonates, fatty alcohol sulfates, fatty acids and sulfated fatty alcohol glycol ethers, furthermore arylsulfonate/formaldehyde condensates, for example condensates of sulfonated naphthalene and naphthalene derivatives with formaldehyde, condensates of naphthalene or of naphtalenesulfonic acid with phenol and formaldehyde, ligninsulfonates, lignin-sulfite waste liquors, phosphated or sulfated derivatives of methylcellulose, and salts of polyacrylic acid.

Antifreeze which can be employed are in principle all those substances which lead to a depression of the melting point of water. Suitable antifreeze comprise alkanoles such as methanol, ethanol, isopropanol, butanols, glycol, glycerine, diethylenglycol and the like.

Thickeners which are suitable are all substances which can be employed for such purposes in agrochemical compositions, for example cellulose derivatives, polyacrylic acid derivatives, xanthan, modified clays and highly-dispersed silicas.

Antifoams which can be employed are all those substances which inhibit the development of foam and which are conventionally used for formulating agrochemical active ingredients. Silicone antifoams and magnesium stearate are particularly suitable.

Preservatives which can be employed are all preservatives used for such purposes in agrochemical compositions. Examples which may be mentioned are dichlorophene, isothiazolenes such as 1,2-benzisothiazol-3(2H)-one, 2-methyl-2H-isothiazol-3-one-hydrochloride, 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one-hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one-calcium chloride complex, 2-octyl-2H-isothiazol-3-one and benzyl alcohol hemiformal.

Stickers/adhesion agents are added to improve the adhesion of the active materials on the seeds after treatment. Suitable adhesives are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers and copolymers derived from these polymers.

In principle, all customary methods of treating or dressing seeds can be employed. Specifically, the treatment follows a procedure in which the seed is mixed with the specifically desired amount of seed dressing formulations, either as such or after previously diluting them with water, using a device which is suitable for this purpose, for example a mixer for solid or solid/liquid components, until the composition is distributed uniformly on the seed. If appropriate, this is followed by drying.

USE EXAMPLE

Example 1

Curative Treatment of Diseased Soybean Plants

In field experiments, different varieties of soybean plants whose leaves were already infested with *Phakopsora pachyrhizi* were treated with an aqueous triticonazole preparation using equipment conventionally used under practice conditions. The application rates were from 20 to 200 g/ha. 25 days after the treatment, the disease level on the untreated, but infested, leaves had developed to such an extent that it covered 50% of the leaf area. In the treated plants, in contrast, *Phakopsora pachyrhizi* disease had only reached a maximum of 25%. This reduced disease level resulted in markedly improved yield in comparison with the untreated control.

Example 2

Protective Treatment of Diseased Soybean Plants

In field experiments, different varieties of soybean plants were treated with an aqueous triticonazole preparation. The application rates amounted to 20 to 200 g/ha. Thereafter, the plants were inoculated with *Phakopsora pachyrhizi*. 25 days after the treatment, the disease level on the untreated, but infested, leaves had developed to such an extent that it covered 50% of the leaf area. In the treated plants, in contrast, *Phakopsora pachyrhizi* disease had only reached a maximum of 25%. This reduced disease level resulted in markedly improved yield in comparison with the untreated control.

Example 3

Seed Treatment

Seed of soybean plants c.v. “Embrapa 48” were treated with a composition suitable for seed treatment, comprising triticonazole as active substance, at application rates in the range of from 12.5 g, 25 g, 50 g, 100 g and 250 g of triticonazole per 100 kg of seed. Thereafter, the seed was sown. The soybean plants thus grown were then inoculated with *Phakopsora pachyrhizi*. After 50 days, the level of rust disease of the leaf areas was determined. The disease level in the plants from untreated seed was at least 50%, whereas the disease level of the leaf area in plants from treated seed was less than 25% in all cases.

Example 4

Protektive Activity of Triticonazole against Soybean Rust Caused by *Phakopsora pachyrhizi* via Seed Treatment A defined amound of a commercial ready-to-used formulation of Triticonazole (suspension concentrate, concentration of active ingredient 200 g/l), corresponding to the desired application (a.r.) rate of 5, 15, 30 und 50 g ai/100 kg soybean was diluted with water to a total volume of 1 Ltr./100 kg Soybean.

Soybean seeds of the cultivar “IAC 8.2” were treated in a commercial device for dressing seeds with the thus prepared aqueous suspension of triticonazole and then seeded in a field experiment in Brazil. The leaves of the soybean plants thus grown were inoculated at an appropriate growing stage with a spore suspension of soybean rust (*Phakopsora pachyrhizi*). Thereafter the plants were kept wet for 6-8 h overnight by means of a finely dripping sprinkling device. During this time the spores germinated and their germ tubes penetrated into the leaf tissue. 60 days after treatment (60 DAT) or seeding, respectively, the extent of rust formation on the leaves of the infected plants was determinated. The results are summarized in table 1:

TABLE 1

| a.r. g/100 kg | % infected leaf area (60 DAT)* |
|---|---|
| 0 (untreated) | 40 |
| 5 | 23 |
| 15 | 11 |
| 30 | 9 |
| 50 | 3 |

Example 5

Curative Activity of Tritconazole against Soybean Rust Caused by *Phakopsora pachyrhizi* via Spray Application A commercial ready-to-used formulation of Triticonazole (suspension concentrate, concentration of active ingredient 200 g/l) was diluted with water to the active ingredient concentraten (act.conc.) given in Table 2.

Leaves of potted soybean seedlings of the cultivar “Hutcheson” were inoculated with a suspension of spores of soybean rust (*Phakopsora pachyrhizi*). The pots were placed in a chamber with high atmospheric humidity (90 to 95%) at 22 to 24° C. for 24 hours. During this time, the spores germinated and the germ tubes penetrated into the leaf tissue. After 3 days, the infected plants were sprayed to runoff point with an aqueous suspension having the concentration of active compound as given in table 2. The suspensions or emulsions were prepared as described above. After the spray coating was dry, the test plants were cultivated in a greenhouse at temperatures between 22 and 24° C. and at 90% relative humidity for 17 days. The extent of the rust development on the leaves was then determined. The results are summarized in table 2.

TABLE 2

| act. conc. ppm | % infected leaf area (17 DAT)* |
|---|---|
| 0 (untreated) | 80 |
| 1 | 9 |
| 4 | 1 |

We claim:

1. A method for controlling rust disease on soybeans, which is rust disease caused by *Phakopsora pachyrhizi* or *Phakopsora meibomiae*, wherein the soybean plants or their seed are treated with an effective amount of (E)-5-(4-chlorobenzylidene)-2,2-dimethyl-1-(1H-1,2,4-triazol-1-ylmethyl)cyclopentanol before or after attack by rust.

2. The method according to claim 1, wherein the seed is treated.

3. The method according to claim 2, wherein (E)-5-(4-chlorobenzylidene)-2,2-dimethyl-1-(1H-1,2,4-triazol-1-ylmethyl)cyclopentanol is employed in an amount of from 1to 500 g per 100 kilograms of seed.

4. The method according to claim 1, wherein the aerial plant parts of the soybean plants are treated.

5. The method according to claim 4, wherein (E)-5-(4-chlorobenzylidene)-2,2-dimethyl-1-(1H-1,2,4-triazol-1-ylmethyl)cyclopentanol is employed in an amount of from 10 to 1000 g/ha.

6. The method according to claim 1, wherein (E)-5-(4-chlorobenzylidene)-2,2-dimethyl-1-(1H-1,2,4-triazol-1-ylmethyl)cyclopentanol is employed jointly with at least one further fungicide from the group of the azole fungicides selected from among epoxyconazole, tebuconazole, fluquinconazole, flutriafol, metconazole, myclobutanil, cycproconazole, prothioconazole and propiconazole.

7. The method according to claim 1, wherein (E)-5-(4-chlorobenzylidene)-2,2-dimethyl-1-(1H-1,2,4-triazol-1-ylmethyl)cyclopentanol is employed jointly with at least one further fungicide from the group of the strobilurins selected from among trifloxystrobin, pyraclostrobin, orysastrobin, fluoxastrobin and azoxystrobin.

8. The method according to claim 1, wherein (E)-5-(4-chlorobenzylidene)-2,2-dimethyl-1-(1H-1,2,4-triazol-1-ylmethyl)cyclopentanol is employed jointly with at least one insecticide from the group of the pyrazole insecticides and the neonictotinoid group.

9. The method according to claim 2, wherein (E)-5-(4-chlorobenzylidene)-2,2-dimethyl-1-(1H-1,2,4-triazol-1-ylmethyl)cyclopentanol is employed jointly with at least one further fungicide from the group of the azole fungicides selected from among epoxyconazole, tebuconazole, fluquinconazole, flutriafol, metconazole, myclobutanil, cycproconazole, prothioconazole and propiconazole.

10. The method according to claim 3, wherein (E)-5-(4-chlorobenzylidene)-2,2-dimethyl-1-(1H-1,2,4-triazol-1-ylmethyl)cyclopentanol is employed jointly with at least one further fungicide from the group of the azole fungicides selected from among epoxyconazole, tebuconazole, fluquinconazole, flutriafol, metconazole, myclobutanil, cycproconazole, prothioconazole and propiconazole.

11. The method according to claim 4, wherein (E)-5-(4-chlorobenzylidene)-2,2-dimethyl-1-(1H-1,2,4-triazol-1-ylmethyl)cyclopentanol is employed jointly with at least one further fungicide from the group of the azole fungicides selected from among epoxyconazole, tebuconazole, fluquinconazole, flutriafol, metconazole, myclobutanil, cycproconazole, prothioconazole and propiconazole.

12. The method according to claim 5, wherein (E)-5-(4-chlorobenzylidene)-2,2-dimethyl-1-(1H-1,2,4-triazol-1-ylmethyl)cyclopentanol is employed jointly with at least one further fungicide from the group of the azole fungicides selected from among epoxyconazole, tebuconazole, fluquinconazole, flutriafol, metconazole, myclobutanil, cycproconazole, prothioconazole and propiconazole.

13. The method according to claim 2, wherein (E)-5-(4-chlorobenzylidene)-2,2-dimethyl-1-(1H-1,2,4-triazol-1-ylmethyl)cyclopentanol is employed jointly with at least one further fungicide from the group of the strobilurins selected from among trifloxystrobin, pyraclostrobin, orysastrobin, fluoxastrobin and azoxystrobin.

14. The method according to claim 3, wherein (E)-5-(4-chlorobenzylidene)-2,2-dimethyl-1-(1H-1,2,4-triazol-1-ylmethyl)cyclopentanol is employed jointly with at least one further fungicide from the group of the strobilurins selected from among trifloxystrobin, pyraclostrobin, orysastrobin, fluoxastrobin and azoxystrobin.

15. The method according to claim 4, wherein (E)-5-(4-chlorobenzylidene)-2,2-dimethyl-1-(1H-1,2,4-triazol-1-ylmethyl)cyclopentanol is employed jointly with at least one further frngicide from the group of the strobilurins selected from among trifloxystrobin, pyraclostrobin, orysastrobin, fluoxastrobin and azoxystrobin.

16. The method according to claim 5, wherein (E)-5-(4-chlorobenzylidene)-2,2-dimethyl-1-(1H-1,2,4-triazol-1-ylmethyl)cyclopentanol is employed jointly with at least one further fungicide from the group of the strobilurins selected from among trifloxystrobin, pyraclostrobin, orysastrobin, fluoxastrobin and azoxystrobin.

17. The method according to claim 2, wherein (E)-5-(4-chlorobenzylidene)-2,2-dimethyl-1-(1H-1,2,4-triazol-1-ylmethyl)cyclopentanol is employed jointly with at least one insecticide from the group of the pyrazole insecticides and the neonictotinoid group.

18. The method according to claim 3, wherein (E)-5-(4-chlorobenzylidene)-2,2-dimethyl-1-(1H-1,2,4-triazol-1-ylmethyl)cyclopentanol is employed jointly with at least one insecticide from the group of the pyrazole insecticides and the neonictotinoid group.

19. The method according to claim 4, wherein (E)-5-(4-chlorobenzylidene)-2,2-dimethyl-1-(1H-1,2,4-triazol-1-ylmethyl)cyclopentanol is employed jointly with at least one insecticide from the group of the pyrazole insecticides and the neonictotinoid group.

20. The method according to claim 5, wherein (E)-5-(4-chlorobenzylidene)-2,2-dimethyl-1-(1H-1,2,4-triazol-1-ylmethyl)cyclopentanol is employed jointly with at least one insecticide from the group of the pyrazole insecticides and the neonictotinoid group.

* * * * *